(12) United States Patent
Delgado et al.

(10) Patent No.: US 7,138,640 B1
(45) Date of Patent: Nov. 21, 2006

(54) METHOD AND APPARATUS FOR PROTECTING SURFACES OF OPTICAL COMPONENTS

(75) Inventors: Gil Delgado, Livermore, CA (US); John McMurtry, Menlo Park, CA (US); James Wiley, Menlo Park, CA (US)

(73) Assignee: KLA-Tencor Technologies, Corporation, Milpitas, CA (US)

( * ) Notice: Subject to any disclaimer, the term of this patent is extended or adjusted under 35 U.S.C. 154(b) by 204 days.

(21) Appl. No.: 10/688,839

(22) Filed: Oct. 16, 2003

Related U.S. Application Data

(60) Provisional application No. 60/419,668, filed on Oct. 17, 2002.

(51) Int. Cl.
*G01J 1/42* (2006.01)
(52) U.S. Cl. .................................... 250/372
(58) Field of Classification Search ............... 250/372, 250/373; 356/237.4, 237.5
See application file for complete search history.

(56) References Cited

U.S. PATENT DOCUMENTS

| | | | |
|---|---|---|---|
| 4,247,203 A | 1/1981 | Levy et al. | |
| 4,391,494 A * | 7/1983 | Hershel | 359/727 |
| 4,556,317 A | 12/1985 | Sandland et al. | |
| 4,618,938 A | 10/1986 | Sandland et al. | |
| 4,845,558 A | 7/1989 | Tsai et al. | |
| 5,031,976 A | 7/1991 | Shafer | |
| 5,488,229 A | 1/1996 | Elliott et al. | |
| 5,529,819 A | 6/1996 | Campi, Jr. | |
| 5,531,857 A * | 7/1996 | Engelsberg et al. | 156/345.5 |
| 5,616,927 A | 4/1997 | Kubota et al. | |
| 5,691,088 A | 11/1997 | Kubota et al. | |
| 5,717,198 A | 2/1998 | Broude et al. | |
| 5,729,325 A | 3/1998 | Kashida | |
| 5,741,576 A | 4/1998 | Kuo | |
| 5,814,381 A | 9/1998 | Kuo | |
| 6,303,196 B1 | 10/2001 | Funatsu | |
| 6,313,467 B1 | 11/2001 | Shafer et al. | |
| 6,368,683 B1 | 4/2002 | Shirasaki | |
| 6,741,394 B1 * | 5/2004 | Tanitsu et al. | 359/619 |
| 6,757,048 B1 * | 6/2004 | Arakawa | 355/30 |
| 6,831,737 B1 * | 12/2004 | Uto et al. | 356/237.4 |
| 2002/0149774 A1 * | 10/2002 | McAninch | 356/445 |

FOREIGN PATENT DOCUMENTS

DE    10062579 A1  *  6/2001

OTHER PUBLICATIONS

Wakamiya, "Status of 157nm Microstepper with High NA Lens," International Sematech, 157nm Technical Data Review dated May 7-9, 2002.

(Continued)

*Primary Examiner*—David Porta
*Assistant Examiner*—David S. Baker
(74) *Attorney, Agent, or Firm*—Beyer Weaver & Thomas, LLP

(57) ABSTRACT

The invention pertains to mechanisms for protecting surfaces of optical components of an optical inspection system. One aspect of the invention relates to a gas purge system that produces a gas stream that blocks contaminants from reaching the optical surfaces of the optical components and that transports contaminants away from the optical surfaces of the optical components. Another aspect of the invention relates to a transparent cover that physically blocks contaminants from reaching the optical surfaces of the optical components. Yet another aspect of the invention relates to a combination of the gas purge system and the transparent cover.

31 Claims, 12 Drawing Sheets

OTHER PUBLICATIONS

Stokowski et al., "Wafer Inspection Technology Challenges for ULSI Manufacturing," KLA-Tencor.

"High-throughput scanning for patterned wafer inspection," http://www.kla-tencor.com/products/defect_control/aitxp.html, downloaded Jun. 11, 2002.

"Automated e-beam inspection," http://www.kla-tencor.com/products/defect_control/es20xp/es20xp.html, downloaded Jun. 11, 2002.

"High-resolution imaging for patterned wafer inspection," http://www.kla-tencor.com/products/defect_control/2351/2351.html, downloaded Jun. 11, 2002.

"2351," Feb. 2001, KLA-Tencor Corporation.

"KLA-Tencor offers 'mix-and-match' of e-beam, UV for wafer inspection," http://www.siliconstrategies.com/story/OEG20000710S0072, downloaded Jun. 11, 2002.

"KLA-Tencor says Samsung cut DRAM development with UV inspection tool," http://www.siliconstrategies.com/story/OEG20010328S0021, downloaded Jun. 11, 2002.

Press Release, "KLA-Tencor and Samsung Complete Joint Wafer Inspection Evaluation For Advanced DRAM Technology Production," http://www.kla-tencor.com/news_events/pr...leases/press_releases2001/9857400002.html, downloaded Jun. 11, 2002.

Stokowski et al., Wafer Inspection Technology Challenges for ULSI Manufacturing—Part II, Yield Management Solutions, Aug. 1999.

* cited by examiner

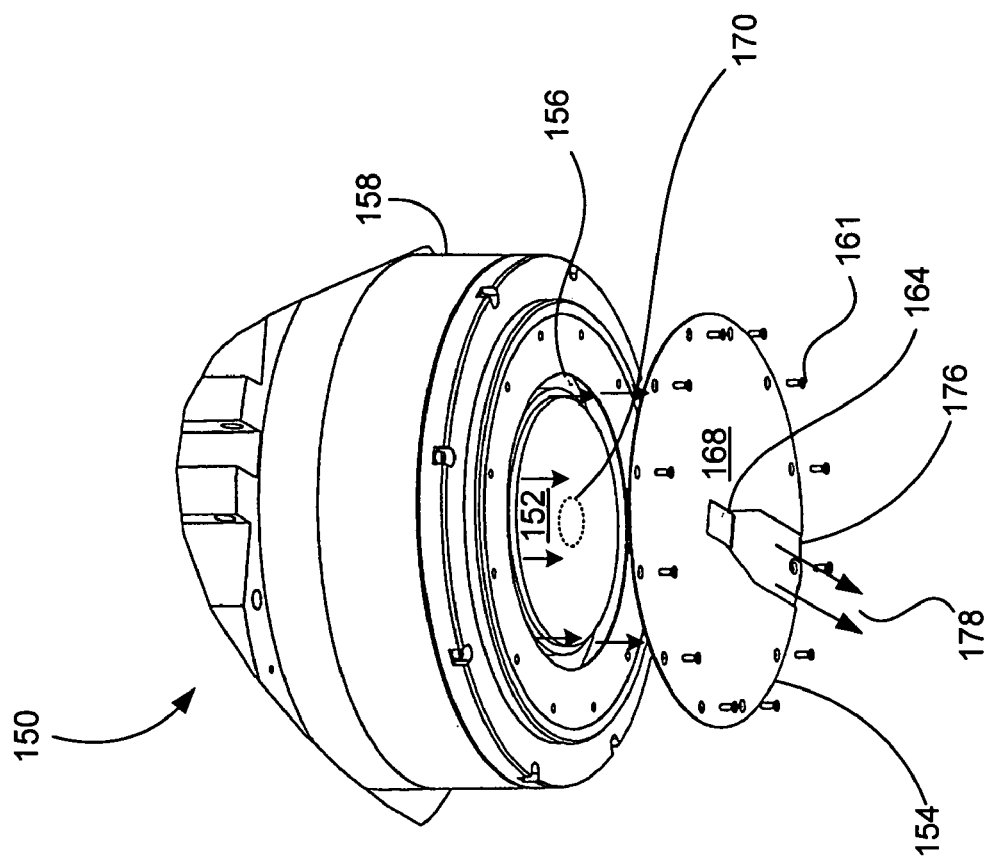
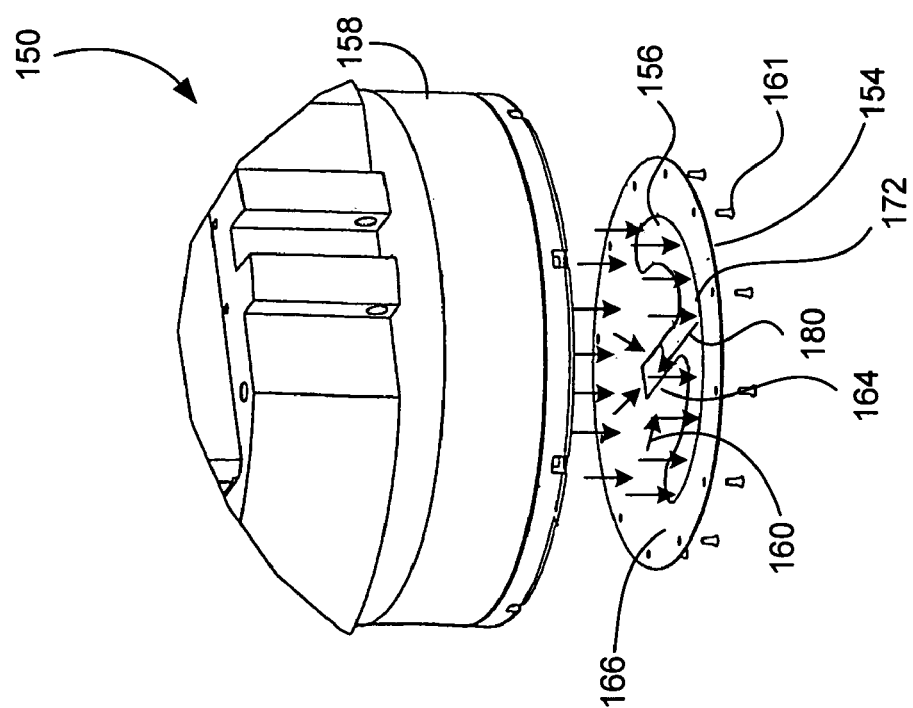
FIG. 5C
FIG. 5B

METHOD AND APPARATUS FOR PROTECTING SURFACES OF OPTICAL COMPONENTS

CROSS REFERENCE TO RELATED APPLICATIONS

This application claims the priority of U.S. Patent Application No. 60/419,668, filed Oct. 17, 2002, entitled "METHOD AND APPARATUS FOR PROTECTING SURFACES OF OPTICAL COMPONENTS" and which is hereby incorporated herein by reference.

FIELD OF THE INVENTION

The present invention relates to optical inspection systems for inspecting a substrate such as reticles, photomasks, wafers and the like. More particularly, the present invention relates to mechanisms for protecting surfaces of optical components of the optical inspection system.

BACKGROUND OF THE INVENTION

Integrated circuits are made by photolithographic processes, which use photomasks or reticles and an associated light source to project a circuit image onto a wafer. The presence of defects on the surfaces of the photomasks, reticles, or wafers are highly undesirable and adversely affect the operation of the resulting circuits. The defects can be due to, but not limited to, a portion of the pattern being absent from an area where it is intended to be present, a portion of the pattern being present in an area where it is not intended to be, chemical deposition or residues from the photomask manufacturing processes which cause an unintended localized modification of the light transmission property of the photomask, artifacts in the photomask substrate such as pits, scratches, and striations, and localized light transmission errors in the substrate or pattern layer.

Defects may also be caused by particulate contaminates such as dust, resist flakes, skin flakes, and erosion of the photolithographic pattern. Conventionally, masks have been protected from such contaminants via a pellicle that is interposed between the light source and the wafer. In most cases, the pellicle is disposed in relatively close proximity to the surface of the mask between the source of light and the mask. Unfortunately, however, the optical components used to distribute the light from the light source are left unprotected.

Although certain types of defects may be prevented, there are many other types of defects that still tend to occur (as described above). These defects have to be found and repaired prior to use in order to maintain a high yield. Methods and apparatus for detecting defects have been around for some time. For example, inspection systems and methods utilizing light have been introduced and employed to various degrees to inspect the surface of substrates such as photomasks, reticles and wafers. These inspection systems and methods generally include a light source for emitting a light beam, optics for focussing the light beam on the surface of the substrate, a stage for providing translational travel, collection optics for collecting either transmitted and/or reflected light, detectors for detecting either the transmitted or reflected light, and a means for constructing a virtual image of the substrate being inspected.

Although such inspection systems work well, there are continuing efforts to improve their designs, as for example, to protect the optical surfaces of the optical components used therein. As should be appreciated, particle contamination that adheres to the optical surfaces may adversely effect the optical quality of the inspection system thereby producing undesirable and/or unpredictable results.

BRIEF DESCRIPTION OF THE DRAWINGS

The present invention is illustrated by way of example, and not by way of limitation.

FIG. 5B is a perspective diagram of the lens system of FIG. 5A, in accordance with one embodiment of the present invention.

FIG. 5C is a reverse perspective view of the lens system of FIG. 5A, in accordance with one embodiment of the present invention.

DESCRIPTION OF THE INVENTION

The invention pertains to mechanisms for protecting surfaces of optical components of an optical inspection system. One aspect of the invention relates to a gas purge system that produces a gas stream that blocks contaminants from reaching the optical surfaces of the optical components and that transports contaminants away from the optical surfaces of the optical components. Another aspect of the invention relates to a transparent cover that physically blocks contaminants from reaching the optical surfaces of the optical components. Yet another aspect of the invention relates to a combination of the gas purge system and the transparent cover.

These and other embodiments of the invention are discussed below with reference to FIGS. 1–15. However, those skilled in the art will readily appreciate that the detailed description given herein with respect to these figures is for explanatory purposes as the invention extends beyond these limited embodiments.

Figure 1:
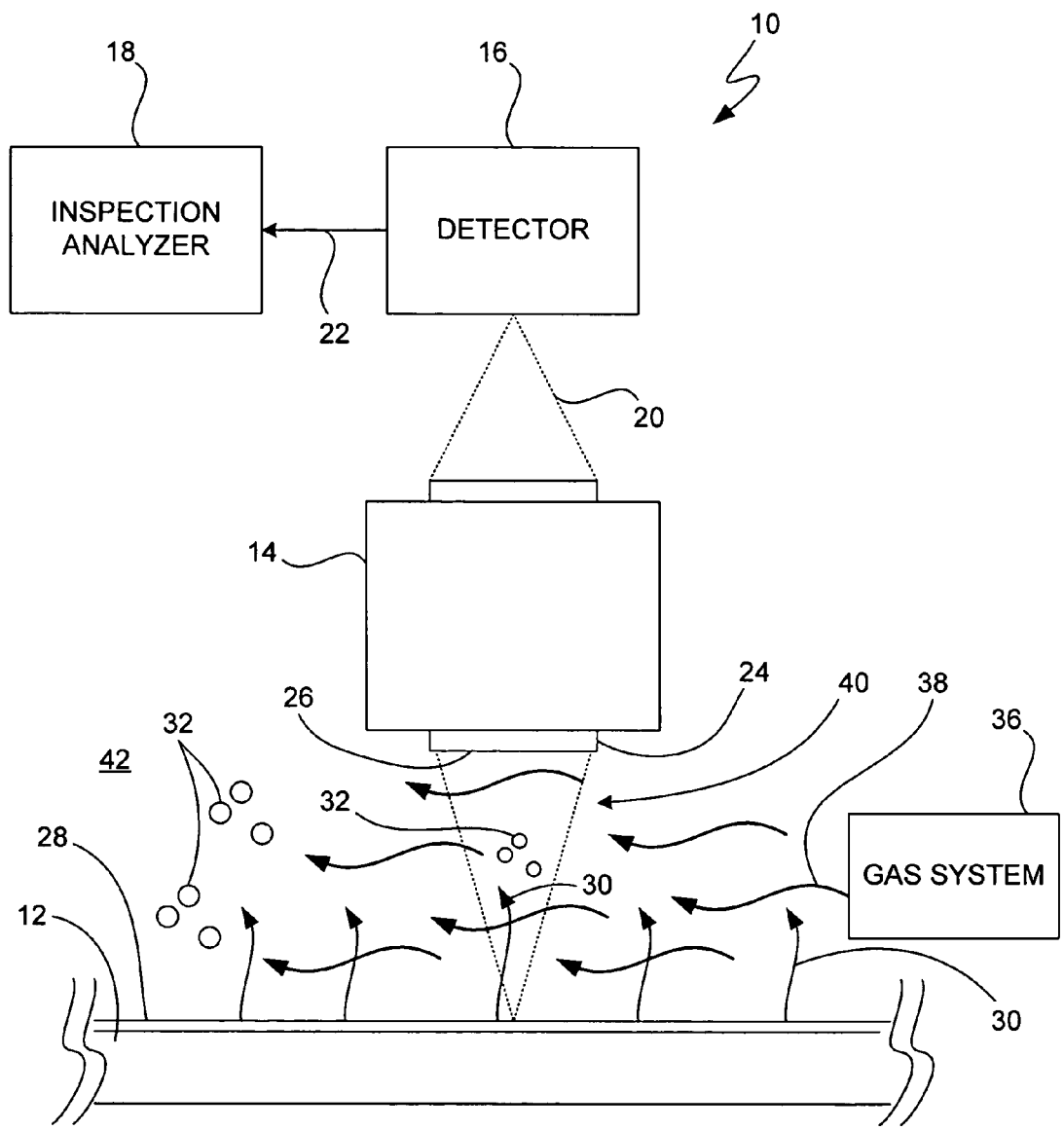
FIG. 1 is a simplified diagram of an optical inspection system, in accordance with one embodiment of the present invention.

FIG. 1 is a simplified diagram of an optical inspection system 10, in accordance with one embodiment of the present invention. As should be appreciated, the dimensions of various components shown in FIG. 1 are exaggerated to better illustrate the components of the optical inspection system 10. The optical inspection system 10 is generally configured to inspect a sample 12 for defects or other abnormalities thereof. The sample may be any suitable device or structure that may be inspected for defects using optical inspection techniques. By way of example, the sample may be associated with semiconductor manufacturing, optical device manufacturing, micro-mechanical device manufacturing, magnetic recording data storage manufacturing and the like. In the illustrated embodiment, the sample corresponds to a substrate such as those used in semiconductor manufacturing. For example, the sample may correspond to wafers, reticles, photomasks, flat panels, and the like.

The optical inspection system 10 generally includes an optical subsystem 14, a detector 16 and an analyzer 18. The optical subsystem 14 is configured to collect light 20 emanating from the sample 12 and to direct the collected light 20 to the detector 16 (shown by the dotted lines). The detector 16 is configured to receive the collected light 20 and to generate an image of at least a portion of the sample 12 with the received light. Further, the analyzer 18 is configured to determine whether there are any defects present on the sample portion by analyzing the image generated by the detector 16, i.e., the output 22 (e.g., resulting image) of the detector 16 is typically fed into the analyzer 18.

With regards to collecting the light, the light emanating from the sample 12 typically results from incident light that scatters, reflects or diffracts upon intersection with the surface of the sample 12. As should be appreciated, the scattered, reflected or diffracted light may indicate the presence of a defect (e.g., particles or voids) or repeating pattern (e.g., targets) on the sample since defects and repeating patterns cause incident light to scatter reflect or diffract in a non trivial manner. The incident light is typically formed with light from a light source (not shown). The light may or may not pass through the optical subsystem 14. That is, the light source may be integrated such that the light travels through the optical subsystem 14 and onto the sample or it may be separated such that light is directed onto the sample without passing through the optical subsystem 14. The light may be in the form of a scanned laser spot, a very large stationary spot (e.g., flood illumination), a scanned line, a stationary line, a scanned substrate, an incoherent source, or the like.

Although not shown in detail herein, the optical subsystem 14 generally includes a plurality of optical components such as lenses, prisms, mirrors, and the like. The optical components are, among other things, arranged to receive and direct the light from the sample 12 to the detector 16. In the illustrated embodiment, the optical subsystem 14 includes a front optical component 24 that has an exposed optical surface 26. In most cases, the front optical component 24 is a lens, however, it should be noted that this is not a limitation and that it may be some other optical component. The front optical component is generally configured for receiving the light emanating from the sample 12.

With regards to generating an image, the detector 16 may include a light detecting arrangement arranged for detecting the light intensity of the collected light, and more particularly for detecting changes in the intensity of light caused by the intersection of the incident light with the sample 12 or it may be a camera such as a CCD array that captures the image of the sample 12 via the light.

With regards to the analyzing the image, a defect may be detected by comparing the received image with a reference image that is either stored in a database or determined in a current or previous step. For example, two areas of the sample 12 having identical features may be compared with respect to each other and any substantial discrepancy may be flagged as a defect. Alternatively or additionally, a defect may be detected by comparing the area under test with corresponding graphics information obtained from a computer aided database system from which the area was derived. In either case, the results of this comparison may be fed as data to an output device or to a data storage unit so that the process may be controlled.

In one particular embodiment of the invention, the optical inspection system 10 is a high resolution UV inspection system based on UV or deep UV light. As should be appreciated, inspection systems have been moving towards using light with shorter wavelengths such as light in the UV or deep UV range in order to resolve very high density integrated circuits (shorter wavelengths are much better for deep submicron inspection). In this embodiment, all the components of the inspection system 10 are configured to handle UV light. For example, the optical subsystem can be adapted for any suitable UV imaging application, such as a UV microscope objective, a collector of surface scattered UV light in a wafer inspection apparatus, or the like. By way of example, the optical inspection system may incorporate UV inspection methods and devices such as those taught in U.S. Pat. No. 6,313,467, which is herein incorporated by reference.

Unfortunately, it has been found that UV light can cause air-borne contaminants such as hydrocarbons, inorganics, moisture, and the like, which are present all over the inspection system to adversely effect the optical surfaces of the optical inspection system. The air borne contaminants may emanate from the fab environment, from the inspection system itself or from the samples being inspected. For example, hydrocarbons may be outgassed from the sample, salts may be produced by photodecomposition of chemical compounds and subsequent formation of anions and cations, silicon compounds may be outgassed from parts glued with silicon based glue, sulfur may be outgassed from metal housings or other parts of the inspection system, and the like.

The high energy photons of UV light generally cause the air borne contaminants to break down into their constituent parts. For example, large hydrocarbon compounds may be broken down into smaller hydrocarbon while silicon glue may outgas into silicon oxides such as siloxun and other silicon oxide compounds. Once the constituent parts are formed, they can act alone or in combination with other constituents to cause optical degradation such as transmission loss. For example, they may form a film (e.g., photodeposits) on the optical surfaces, which may be cleaned in a subsequent process or they may destroy the optical surface altogether. Either way, the operation and/or performance of the inspection system is typically impaired. For example, inspection instabilities, which effect the accuracy of the inspection system, may be created, as for example, via loss of transmission, non-uniformity of illumination, blemishes, scattering (increased and variable and background light), and the like.

To elaborate, the constituent parts can adhere to almost anything and since the constituent parts are formed in the region of the UV light they tend to adhere to surfaces proximate to where the UV light travels, as for example, the optical surfaces of the optical components used to transport the light. Overtime, they may gradually build up a film on the optical surfaces thereby diminishing the optical performance of the system. For example, the deposits may distort the collected light thereby producing undesirable and/or unpredictable inspection results.

Some of the constituent parts that adhere to the optical surfaces may be cleaned off while other constituents that adhere to the optical surfaces may be permanent, i.e., cannot be cleaned off. For example, deposits of carbon, which are formed from broken down hydrocarbons can be cleaned off while deposits of silicon oxides (glass), which are formed by outgassing of siloxanes and other silicon oxides and moisture (e.g., hydrogen and oxygen), cannot be cleaned off thus destroying the optical components. Furthermore, the constituent parts may create chemicals that attack the optical surfaces. For example, sulfuric acid, which is formed by adding moisture to sulfur, may etch the optical coatings thus destroying the optical components.

By way of example and referring to FIG. 1, the sample 12 may have a layer of photoresist 28 baked thereon. Although the baked photoresist 28 is somewhat inert, it still tends to outgas air born contaminants 30 such as hydrocarbons. As shown in FIG. 1, the UV light 20 breaks down the air borne contaminants 30 into their constituent parts 32, and some of the constituent parts 32 deposit on the optical surface 26 of the optical component 24 thereby degrading the optical characteristics of the optical component 24.

In accordance with one aspect of the present invention, the contaminants, as well as the constituent parts formed therefrom, are controlled by flowing a clean gas in the inspection system. In particular, the optical components of the UV inspection system are protected from harmful contaminants by flooding a gas inside the UV inspection system around the optical components. The gas flow is generally configured to prevent the contaminants from bombarding the optical surfaces of the optical components. The gas flow also collects and removes the contamination from a UV region of the inspection system, as for example, in front of the optical component. As a result removing the contamination from the UV region, the particles that typically degrade the optical surfaces of the optical components can be reduced.

Referring to FIG. 1, the optical inspection system 10 may include a gas flow system 36 configured to continuously flow a gas stream 38 through the inspection system 10, and more particularly in regions surrounding the optical surface 26 of the optical component 24 of the optical subsystem 14 so as to prevent the constituent parts 32 from reacting with the optical surface 26. As such, the need for replacing or cleaning the optical components is reduced. Further, a constant optical condition is obtained, rather than one that changes as a function of substrates processed.

The gas stream 38 is generally configured to prevent the contamination 30 from diffusing up to the optical surface 26 of the optical component 24. The gas stream 38 is also configured to flush the contamination 30 as well as the constituent parts 32 away from the optical surfaces 26. For example, the gas stream 38 may collect and remove contaminants 30 that are diffusing towards the optical surfaces 26 and the constituent parts 32 that are formed therefrom. In most cases, the gas stream 38 is disposed in UV regions 40 of the inspection system 10, i.e., areas where UV light travels. The UV regions may be located anywhere along the optical path of the optical subsystem 14, as for example, between the sample under inspection and the front optical component, between adjacent optical components within the optical subsystem, between optical components and detectors, and the like.

In the illustrated embodiment, the UV region 40 is the region between the sample 12 and the optical surface 26 of the optical component 24, i.e., where the light emanating from the sample 12 is scattered, reflected, or diffracted. As shown, the gas stream 38 is flowed into and out of the UV region 40 so that the contaminants can be transported from the UV region 40 to a non UV region 42 located away from the UV region 40. That is, as the gas flows through the UV region 40, it collects the contaminants 30 that are proximate thereto and transports them outside the UV region 40. The route that the gas stream 38 follows through the UV region 40 may be widely varied. For example, the gas stream 38 may be routed across the exposed optical surface 26 transverse to the optical axis of the optical surface 26 (as shown) and/or it may be routed away from the exposed optical surface 26 substantially parallel to the optical axis of the optical surface 26. The gas stream may be symmetrical or asymmetrical. It should be understood that collecting contaminants is not limited to the UV region and that collecting may occur in non UV regions as well, for example, collecting may occur throughout the inspection system.

The gas flow system 36 may be widely varied. For example, the gas flow system 36 may include a blower arrangement for blowing the gas through the UV region 40, a vacuum arrangement for sucking the gas through the UV region 40 or a pressurized gas source for forcing the gas through the UV region 40. By way of example, the blower arrangement may include injectors for injecting gas at various pressures (high, medium, low) and the vacuum arrangement may include vacuum ports for sucking air at various vacuum pressures. The pressurized gas source is generally preferred since it can provide a clean gas. By way of example, the gas may be nitrogen ($N_2$), and the like. The pressurized gas source may be a small individual pressure tank or it may be a large pressurized tank such as those used in manufacturing plants. The volume of gas produced by the any of these arrangements, as well as the flow rate, is typically configured to block contaminants as well as to carry the contaminants away before they reach the optical surface 26.

Figure 2:
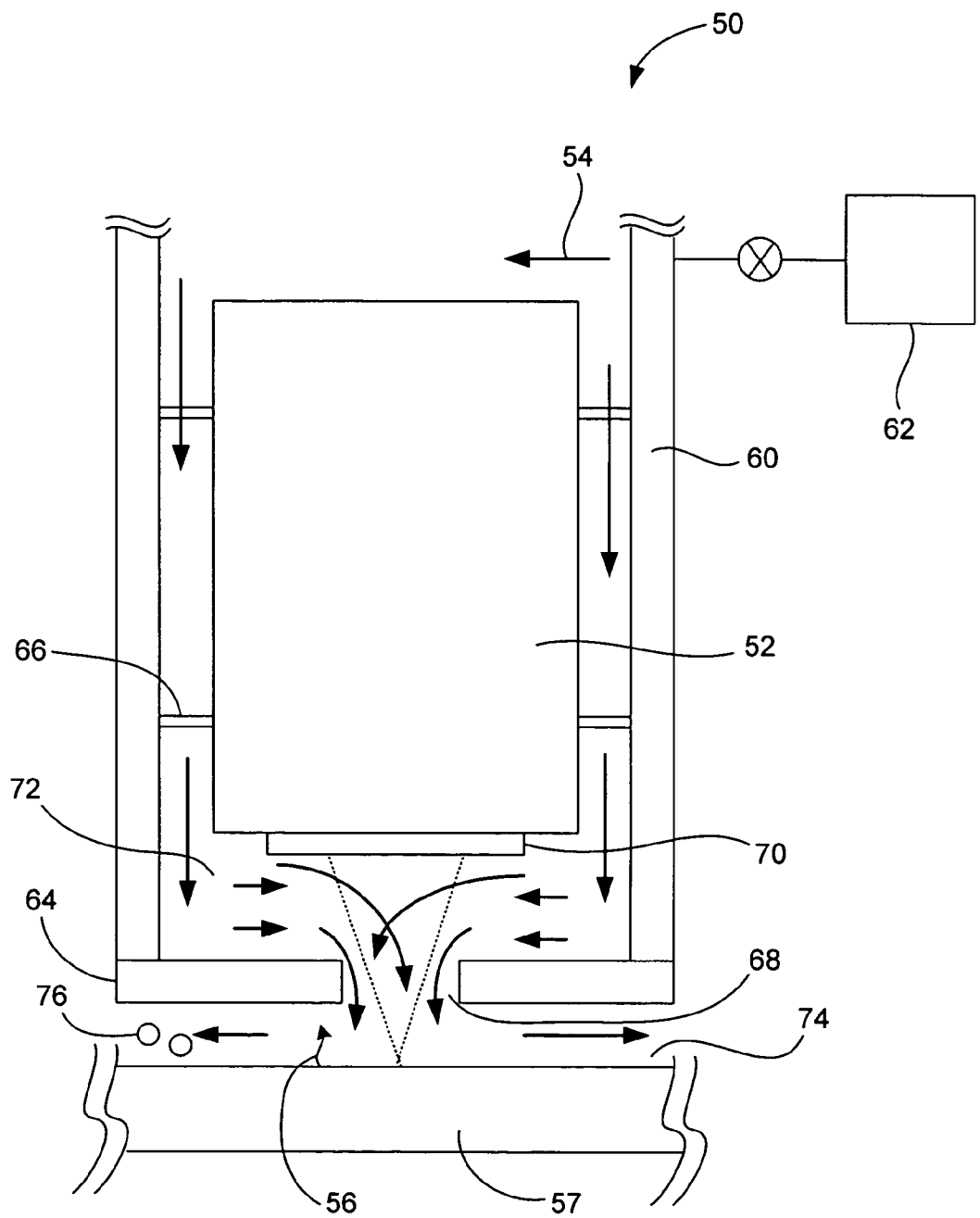
FIG. 2 is a diagram of a gas flow system, in accordance with one embodiment of the present invention.

FIG. 2 is a diagram of a gas flow system 50, in accordance with one embodiment of the present invention. The gas flow system 50 is configured to flood areas of an optical system 52 with a gas 54 so as to prevent volatile contaminants 56 from adversely effecting sensitive optical surfaces of optical components contained within the optical system 52. By way of example, the optical system 52 may be an optical system associated with a UV inspection system, which is capable of inspecting a substrate 57 such as a wafer, reticle or mask with UV light. The gas flow system 50 includes a housing 60, a pressurized gas source 62 and a cover 64. The housing 60 is configured to surround the optical system 52, i.e., the housing provides a space within which the optical system may be placed. The housing 60 serves to protect the optical system 52 from external elements as well as to provide a conduit for the gas 54. The housing 60 is typically formed from materials that do not outgas harmful contaminants, as for example, metals such as stainless steel.

The optical system 52 is supported within the housing 60 via a plurality of supports 66. The supports 66 may be positioned in any manner, however, they are generally positioned in a symmetric manner about the periphery of the optical system 52. In some cases, the supports may fill the space between the optical system 52 and the inner periphery of the housing 60. In cases such as these, the supports 66 may have a plurality of holes that allow the passage of gas therethrough. The holes typically provide a symmetrically availability of gas therethrough. Because of the sensitivity of the optical components of the optical system 52, the supports 66 may correspond to flexures that help to maintain the proper position of the optical components for various conditions (e.g., temperatures, vibrations, and the like).

The pressurized gas source 62 is configured to supply pressurized gas to the space defined by the housing 60, i.e., the space in which the optical system is contained. That is, the pressurized air source 62 is fluidly coupled to the housing 60 such that the gas source 62 may introduce gas 54 into the space within the housing 60. By way of example, the pressurized gas may be any clean gas such as $N_2$, and the like.

The cover 64 is connected to the housing 60. The cover 64 serves to protect the optical system 52 from external elements as well as to provide a conduit for the gas 54. The cover 64 is typically formed from materials that do not outgas harmful contaminants such as organic or inorganic molecules. The cover 64 typically includes an opening 68 through which the optical system 52 works. The size of the opening 68 generally corresponds the size of the optical path needed for collecting light emanating from a particular area of the substrate 57. As shown, the cover 64 is spaced apart from the optical system 52. For example, the cover 64 may be spaced apart from a front lens 70 of the optical system 52. The optical system 52 and the cover 64 therefore define a first conduit 72 therebetween. The cover 64 is also spaced apart from the substrate 57. As such, the cover 64 and the substrate 57 form a second conduit 74 therebetween.

The combination of the above elements is configured to control the environment around the optical system 52 so as to prevent contaminants from bombarding the optical surfaces of the optical system 52, as for example the front lens 70. This is generally accomplished by flowing the gas 54 through the housing 60 and out the opening 68 in the cover 64. As shown, the gas 54 flows through gaps or holes formed between the various supports 66 (the gas may also flow through the optical system itself) and then around the optical system 52 and into the first gas conduit 72. Once in the first gas conduit 72, the gas 54 flows to the opening 68 in the cover 64 where it exits the housing 60. During this time, the gas 54 provides a gas stream that substantially blocks contaminants from reaching the front lens 70 of the optical system 52. Once the gas 54 exits the housing 60, it flows through the second gas conduit 74. During this time, any contaminants 76 that are in the way of the gas stream in the first gas conduit 72 are carried away in the second gas conduit 74. In essence, the second conduit 74 serves as exhaust port for removing the contaminants 76 from around the front lens 70.

Figure 3A:
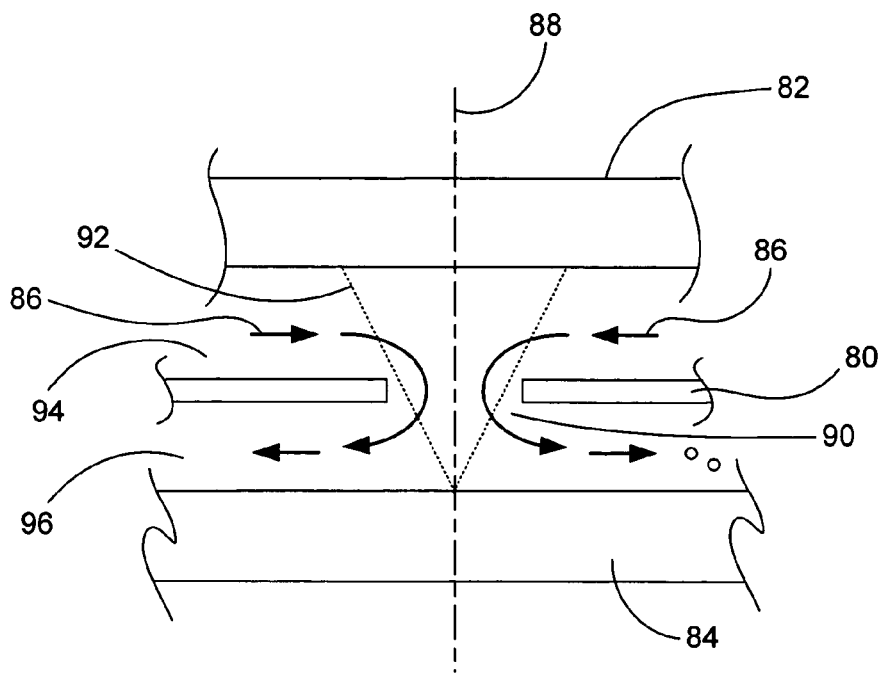
FIG. 3A is a broken away side view of the cover showing its position relative to a lens and a substrate to be inspected, in accordance with one embodiment of the present invention.
Figure 3B:
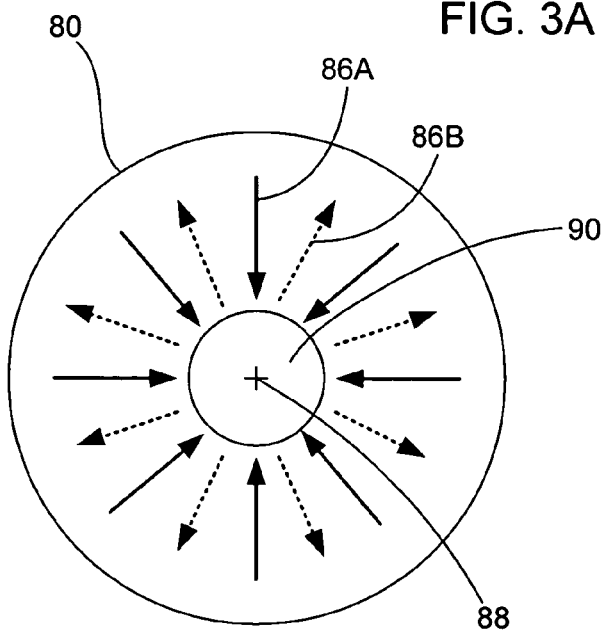
FIG. 3B is a top view of the cover showing the distribution of gases therethrough, in accordance with one embodiment of the present invention.
Figure 3C:
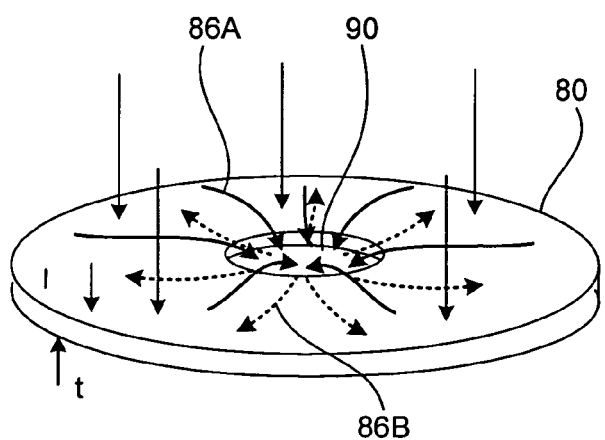
FIG. 3C is a perspective view of the cover showing the distribution of gases therethrough, in accordance with one embodiment of the present invention.

FIGS. 3A–C are diagrams of a cover 80, in accordance with one embodiment of the present invention. By way of example, the cover 80 may generally correspond to the cover shown in FIG. 2. FIG. 3A is a broken away side view of the cover 80 showing its position relative to a lens 82 and a substrate to be inspected 84, FIG. 3B is a top view of the cover 80 showing the distribution of gases therethrough and FIG. 3C is a perspective view of the cover 80 showing the distribution of gases therethrough. In this particular embodiment, the cover 80 is configured to generate a symmetrical gas flow 86 for preventing contaminants from adversely effecting the lens 82. By symmetrical, it is generally meant that the gas flow 86 is balanced in all directions. For example, the gas flow 86 is distributed equally from all sides towards and away from the optical axis 88. As shown, the cover 80 includes an opening 90 through which the symmetrical gas flow 86 flows. The opening 90 also provides room for light 92 to be collected by the lens 82.

Referring to FIG. 3A, the cover 80 is configured to form first and second conduits 94 and 96 respectively, between the lens 82 and the substrate to be inspected 84. The first conduit 94 is configured to direct the gas to the opening 90 so that the gas can flow to the second conduit 96. In this particular embodiment, the gas flow 86 curves around the edges within the opening 90 of the cover 80 such that the direction of the gas flow 86B through the second conduit 96 is substantially opposite the gas flow 86A through the first conduit 94, i.e., the gas flow takes a tight turn around the edge of the cover. As should be appreciated, the gas flow 86 flowing through the opening 90 produces a gas stream that is directed away from the lens 82. Once outside the opening 90, the gas stream begins to flow through the second conduit 96 thus forcing any contaminants away from the lens 82. In one implementation, the top surface of the cover 80 is spaced apart an equal distance away from the lens 82, and the bottom surface of the cover 80 is spaced apart an equal distance away from the substrate 84 in order to produce a more symmetrical gas flow.

Referring to FIGS. 3B and 3C, the cover 80 via the first and second conduits is configured to form first and second gas streams 86A and 86B. The first stream 86A, i.e., the top stream as seen in FIG. 3A, is shown by solid lines while the second stream 86B, i.e., the bottom stream as seen in FIG. 3A, is shown by dotted lines. As shown, the first stream 86A is directed toward the optical axis 88 while the second stream 86B is directed away from the optical axis 88. The first gas stream 86A forces the contaminants away from the lens 82, e.g., towards the opening 90, while the second stream 86B forces the contaminants away from the inspection area altogether. In one implementation, the thickness, t, of the cover is uniform throughout in order to produce a more symmetrical gas flow.

Figure 4A:
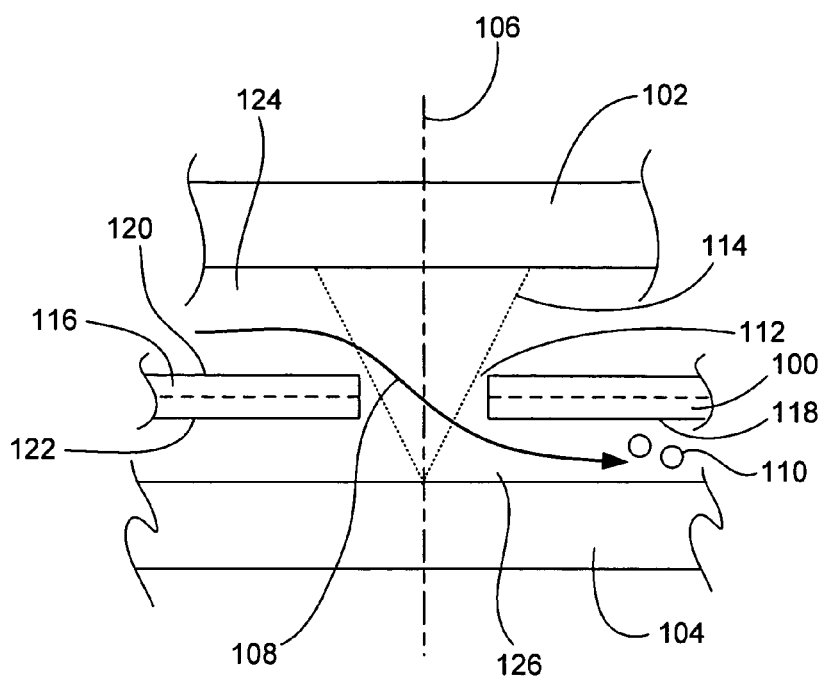
FIG. 4A is a broken away side view of the cover showing its position relative to a lens system and a substrate to be inspected, in accordance with one embodiment of the present invention.
Figure 4B:
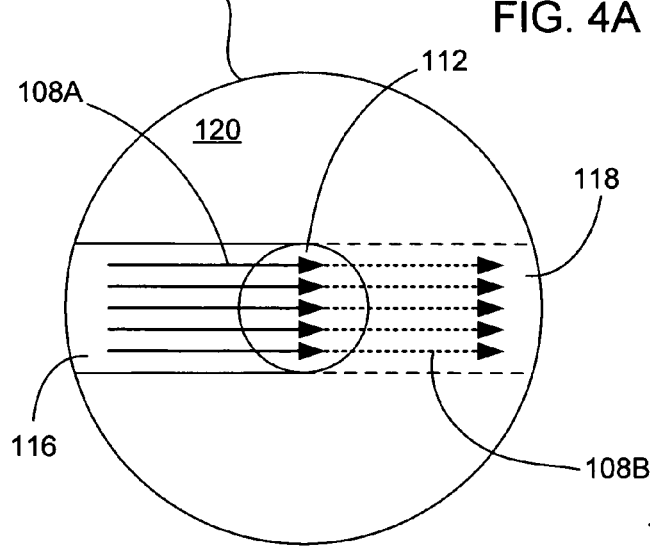
FIG. 4B is a top view of the cover showing the distribution of gases therearound, in accordance with one embodiment of the present invention.
Figure 4C:
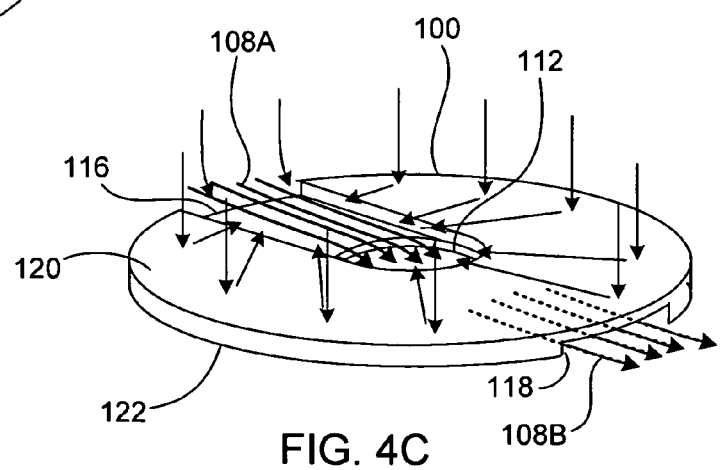
FIG. 4C is a perspective view showing the distribution of gases therethrough, in accordance with one embodiment of the present invention.

FIGS. 4A–C are diagrams of a cover 100, in accordance with another embodiment of the present invention. By way of example, the cover 100 may generally correspond to the cover shown in FIG. 2. FIG. 4A is a broken away side view of the cover 100 showing its position relative to a lens 102 and a substrate to be inspected 104, FIG. 4B is a top view of the cover 100 showing the distribution of gases therearound and FIG. 4C is a perspective view of the cover 100 showing the distribution of gases therethrough. In this particular embodiment, the cover 100 is configured to form an asymmetrical gas flow. By asymmetrical, it is generally meant that the gas flow is not balanced in all directions. For example, the gas flow is the not the same (not equal) on opposite sides of the optical axis 106. More particularly, the cover 100 is configured to generate a lateral gas stream 108 that travels across the optical axis 106 of the lens 102 (substantially parallel to the lens and substrate). The lateral gas stream 108 essentially forms a wall that blocks contaminants from reaching the lens 102. The lateral gas stream 108 also sweeps contaminants 110 away from the lens 102. As should be appreciated, asymmetrical flow patterns such as these overcome static or dead centers (no flow in the center) such as those found in some symmetrical flow patterns.

Referring to all the FIGS. 4A–C, the cover 100 includes an opening 112 that provides a passageway for the gas stream 108 and that provides room for the light 114 to be collected by the lens 102. The cover 100 also includes a first channel 116 and a second channel 118, each of which helps control the flow of gas through the opening 112. The first and second channels 116 and 118 are recessed in the top and bottom surfaces of the cover 100. The first channel 116 is recessed in the top surface 120 of the cover 100 and the second channel 118 is recessed in the bottom surface 122 of the cover 100. The first channel and second channels 116 and 118 are also positioned on opposing sides of the opening 112. That is, the first channel 116 is located on one side of the opening 112 and the second channel 118 is located on the other side of the opening 112, i.e., mirror images of each other. The first and second channels 116 and 118 generally have central axes that are aligned with one another.

Referring to FIG. 4A, the cover 100 is configured to form first and second conduits 124 and 126 respectively between the lens 102 and the substrate to be inspected 104. The first conduit 124 provides a passageway to the opening 112 so that the gas can flow to the second conduit 126. The second conduit 126 provides a passageway away from the opening 112 so that the gas can be exhausted. In this particular embodiment, the first and second channels 116 and 118 are configured to direct the gas stream 108 in a particular direction such that the gas stream 108 flows laterally across the lens 102 from the first conduit 124 to the second conduit 126, i.e., the gas flow cuts across the optical axis 106. That is, the first channel 116 forces the gas stream 108 across the opening 112 and the second channel 118 collects the gas stream 108 and forces it away from the opening 112. As shown, the direction of the gas flow through the second conduit 126 is substantially the same as the gas flow through the first conduit 124. Once outside the opening 112, the gas stream 108 begins to flow through the second conduit 126 thus forcing any contaminants 110 away from the lens 102.

Referring to FIGS. 4B and 4C, the gas stream 108 is shown having a top stream 108A and a bottom stream 108B (the top stream is shown by solid lines while the bottom stream is shown by dotted lines). It should be noted however, that this is for ease of discussion since the gas stream is really a continuous stream. The top stream 108A generally refers to the portion of the gas stream that flows through the first channel 116, and the bottom stream 108B generally refers to the portion of the gas stream that flows through the second channel 118. As should be appreciated, the top and bottom streams flow in the same general direction. To elaborate, the channels 116 and 118 form low resistance low pressure zones while the raised surfaces (top and bottom surface) around the channels 116 and 118 form high resistance high pressure zones. As should be appreciated, where there is a restriction there tends be high pressure and low flow, and where there is not a restriction (or less of a restriction) there tends to be low pressure and high flow. The gas stream 108 tends to follow the path of least resistance, thus the gas stream 108 tends to flow into and within the channels 116 and 118. The channels sort of serve as a plenum to pick up as much of the gas input as possible and then channel it across and then out. In so doing, the gas stream 108 forms a gas wall across the opening that serves to protect the optical surface of the lens.

The shape of the channels 116 and 118 may be widely varied. For example, they may be rectilinear (as shown) or they may be curvilinear (e.g., neck shape). Furthermore, the first and second channels 116 and 118 may have a similar configuration or they may have a different configuration. For example, the first channel 116 may have a rectilinear shape and the second channel 118 may have a curvilinear shape. Additionally, the thickness of the cover at the first channel may be similar (as shown) or different than the thickness of the cover at the second channel.

Referring to FIGS. 5A–E, a specific implementation of a purging UV lens system 150 will be described in detail, in accordance with one embodiment of the present invention. The UV lens system 150 is configured to be placed in a UV optical inspection system that is capable of inspecting substrates 151 such as wafers, reticles, masks and the like. The UV lens system 150 typically includes a front lens 152 that is configured to operate under a high flux of UV or DUV. The front lens 152 is therefore susceptible to photocontamination at the exterior surface thereof. In order to prevent photocontamination, the purging UV lens system 150 is generally configured to flood the area in front of the front lens 152 with a clean purging gas. More particularly, the UV lens system 150 includes a lens cover 154 that is configured to create a clean gas curtain across the high UV/DUV center of lens (e.g., imaging zone) with an initial clean purge gas flow distributed through the UV lens system 150.

Figure 5A:
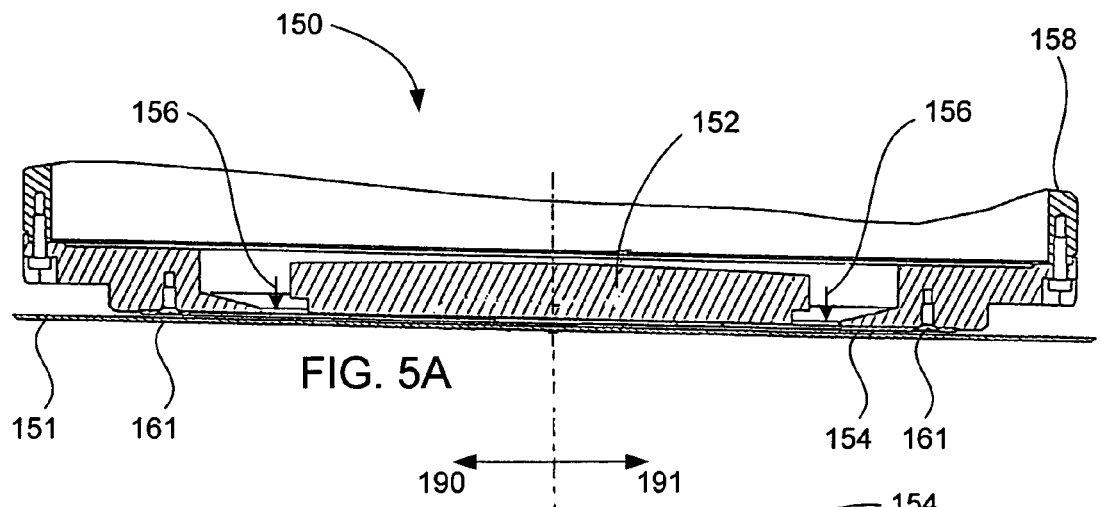
FIG. 5A is a side elevation view of a lens system with a cover attached thereto, in accordance with one embodiment of the present invention.

Referring to FIGS. 5A–C, the clean purge gas is initially distributed around the periphery of the front lens 152. The initial clean purge gas, which is designated 156, generally flows between a lens housing 158 and the various optical components of the lens system contained within the housing (which are not shown). In most cases, the flow of the initial clean purge gas 156 is radially symmetric around the front lens 152, i.e., the initial clean purge gas 156 is distributed evenly around the periphery of the front lens 152. The flow of the initial clean purge gas 156 is typically kept moving at low pressure. After flowing past the periphery of the lens 152, the initial clean purge gas 156 is redirected by the presence of the lens cover 154. The redirected clean purge gas, which is designated 160, generally flows between the lens 152 and the lens cover 154. As shown, the lens cover 154 is capable of being attached to the lens housing 158. The means of attachment may be widely varied. In the illustrated embodiment, the lens cover 154 is attached to the housing 158 via a plurality of screws 161.

Referring to FIGS. 5B–C, the lens cover 154 includes an opening 164, an upper surface 166 and a lower surface 168. The upper surface 166 is capable of interfacing with the lens housing 158 so that the lens cover 154 may be attached thereto. When attached, the upper surface 166 faces the front lens 152, the lower surface 168 faces the substrate 151 and the opening 164 is positioned in front of the imaging zone 170 of the front lens 152. As shown in FIG. 5B, the upper surface 166 includes a collection area 172 for collecting the initial clean purge gas 156 and a directing area 174 for redirecting the collected gas to the opening 164. The collection area 172 and the directing area 174 are typically recessed within the upper surface 166 thereby forming a "collection volume" and a "directing volume" respectively. As shown in FIG. 5C, the lower surface 168 includes an exit area 176 for collecting the gas passing through the opening 164 and for directing the gas, which is designated 178, to an exhaust area outside the periphery of the lens cover 154. The exit area 176 is typically recessed within the lower surface 168 thereby forming an "exit volume".

Figure 5E:
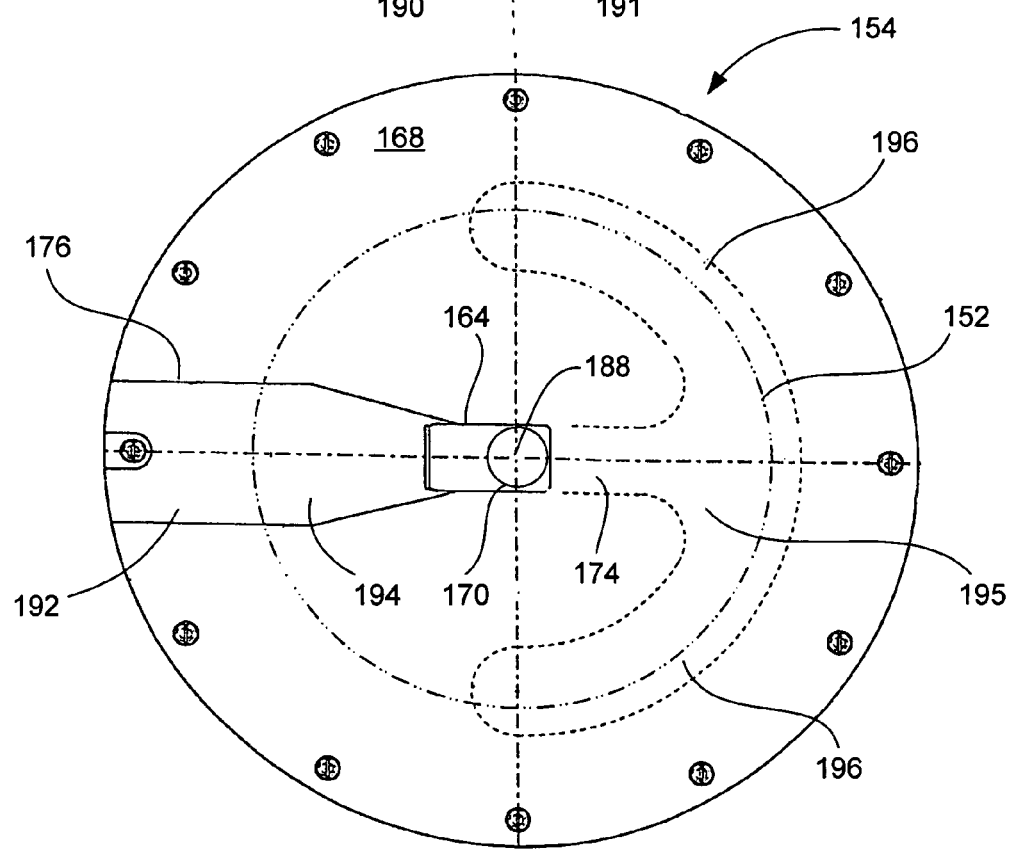
FIG. 5E is a bottom view of the lens system of FIG. 5A, in accordance with one embodiment of the present invention.
Figure 5D:
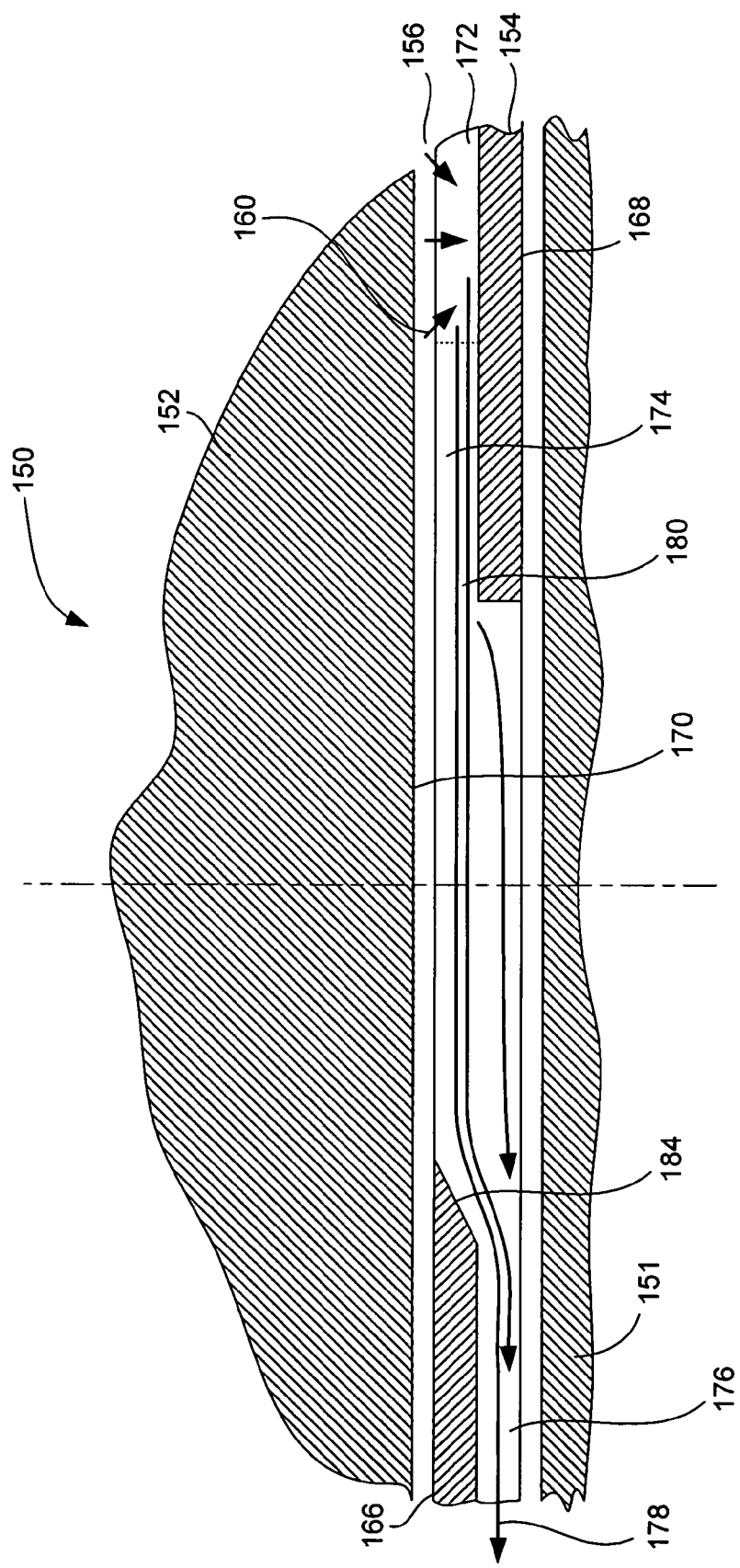
FIG. 5D is a close up side elevation view of the lens system of FIG. 5A, in accordance with one embodiment of the present invention.

Referring to FIGS. 5B–D, the purge gas 156 is distributed with radial symmetry around the lens cover 154. The upper surface 166 after receiving the purge gas 156, constricts the gas flow thus forcing the gas 160 towards the opening 164 and collection area 172. The collection area 172, on the other hand, promotes gas flow thus forcing the gases 156 and 160 to flow therein. As shown, the gases 156 and 160 tends to flow to one side of the lens cover since the collection area 172 is only disposed on one side of the lens cover 154. The directing portion 174, which is coupled to the collection area 172, organizes the collected gas and directs it in substantially one direction (the directed gas is generally designated 180). The direction is generally opposite the side of the lens cover 154 having the collection area 172. As shown, the directing portion 174 directs the gases 180 towards the exit area 176 across the optical axis and in front of the imaging zone 170 of the front lens 152. The exit area 176, which is located directly across from the directing area 174, allows the directed gas to flow from the upper surface 166 to the lower surface 168 of the lens cover 154. The exit area 176 also allows the gas to escape to outside the radius of the lens cover 154. As shown in FIG. 5D, the exit area 176 may include a knife feature 184 configured to help force the gas into the exit area 176, i.e., the knife feature 184 helps to capture and thus collect the directed gas flow.

Referring to FIG. 5D, the thickness, t, of the lens cover may be widely varied. In one particular implementation, the thickness, t, of the lens cover 154 is about 0.8 mm. The depth of the collection, directing and exit areas may also be widely varied. In one particular implementation, the depth of the collection and directing areas is about 0.3 mm and the depth of the exit area is about 0.5 mm. The first space between the upper surface 166 of the lens cover 154 and the lens 152 as well as the second space between the lower surface 168 of the lens cover 154 and the substrate 151 may also be widely varied. In one particular implementation, the upper surface 166 is positioned about 0.2 mm from the lens 152 and the lower surface 168 is positioned about 0.5 mm from the substrate 151.

Referring to FIG. 5E, the lens cover 154 will be described in greater detail. FIG. 5E is a bottom view of the lens cover 154 and therefore the elements of the lower surface are shown with solid lines and the elements of the upper surface are shown with dotted lines. The outer periphery of the lens 152, which is located on the other side of the lens cover 154, is also shown by way of dotted lines. The imaging zone 170, which is located within the opening 164, is shown by cross hatching. As shown, the lens cover 154 is centered along the optical axis 188 of the lens 152 and more particularly the imaging zone 170.

The opening 164 is positioned in the center of the lens cover 154 so that the imaging zone 170 fits therethrough. The size and shape of the opening 164 may also be widely varied. For example, the opening 164 may be circular, square, rectangular, and the like. In the illustrated embodiment, the opening 164 is rectangular. The size generally depends on the size of the imaging zone 170, i.e., the opening is configured to allow light to travel between the imaging zone and the substrate. The opening 164 may be symmetrical or asymmetrical. In the illustrated embodiment, the opening 164 is asymmetrical since a portion of the opening 164 is skewed towards a first side 190 of the lens cover 154. The exit area 176, which is located on the first side 190 of the lens cover 154 abuts the skewed portion of the opening 164. The size and shape of the exit area 176 may also be widely varied. For example, the exit area 176 may be a parallel channel, a flared channel, a necked channel or the like. In the illustrated embodiment, the exit area 176 is a combination of a parallel and flared channel 192 and 194 respectively. The flared channel 194 helps to receive the gas flow from the opening 164 and to further direct the gas flow away from the opening 164. The parallel channel 192 helps to direct the gas flow outside the periphery of the lens cover 154.

The directing area 174, which is located on a second side 191 of the lens cover 154, abuts the side of the opening 164 that is opposite the exit area 176. The size and shape of the directing area 174 may be widely varied. For example, the directing area 174 may be a parallel channel, a flared channel, a necked channel or the like. In the illustrated embodiment, the directing area 174 is a parallel channel that has substantially the same width as the opening 164.

The collection area 172, which is also located substantially on the second side 191 of the lens cover 154, abuts the side of the directing area 174 that is opposite the side that abuts the opening 164. The collection area 172 generally includes a feeding portion 195 and a capturing portion 196. The capturing portion 196 is configured to collect as much gas as possible and the feeding portion 195 is configured to feed the collected gas to the directing area 174. The size and shape of the feeding and capturing portions 195 and 196 may be widely varied. In the illustrated embodiment, the capturing portion 196 generally flares out along the periphery of the lens cover 154 (thereby forming a semi annular channel) while the feeding portion 195 flares into the directing area 174. This shape is believed to help to direct the gas flow to one side of the lens cover 154 so that the gas flow may be directed in substantially one direction towards the opening 164. As shown, the peripheral regions of the capturing portion 196 are generally located outside the periphery of the lens 152 so that initial gas purge can be readily collected.

Figure 6:
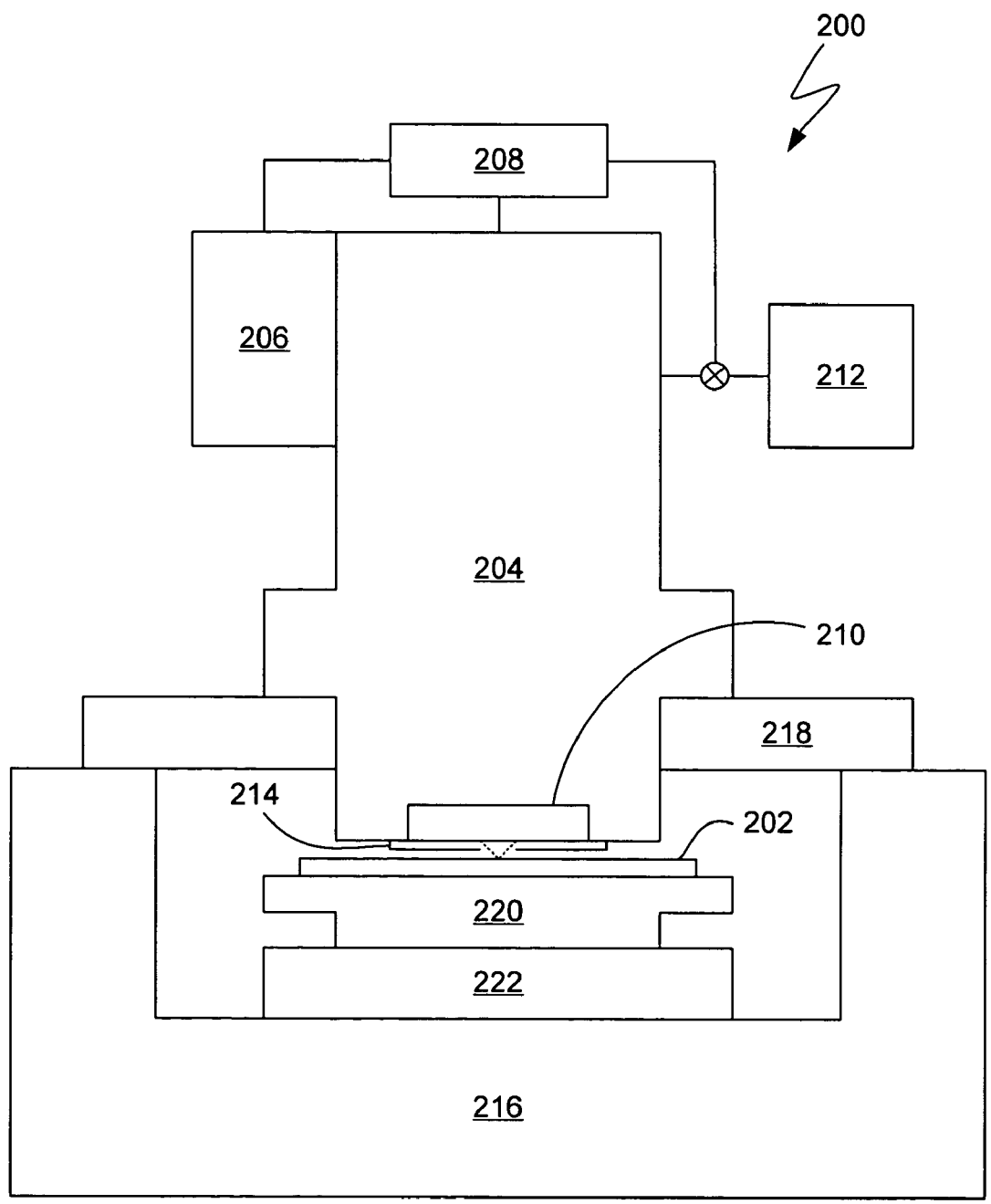
FIG. 6 is a simplified diagram of a UV optical inspection system, in accordance with one embodiment of the present invention.

FIG. 6 is a simplified diagram of a UV optical inspection system 200, in accordance with one embodiment of the present invention. The UV optical inspection system 200 is configured to inspect substrates 202 for defects using UV light. By way of example, the substrate 202 may correspond to semiconductor wafers, reticles, masks and the like. The UV optical inspection system 200 generally includes a lens system 204, a camera 206 and a controller 208. The lens system 204, which includes a front lens 210 for receiving UV light from the substrate 202, is configured to collect light emanating from the substrate 202 and to direct the light to the camera 206. The camera 206 is configured to receive the light from the lens system 204 and to form an image of a portion of the substrate 202. The camera 206 is also arranged to feed the image to the controller 208. The controller 208 is configured to control the various components of the inspection system 200. The controller 208 typically includes an analyzer for receiving the image from the camera 206, constructing a virtual image of the substrate surface based on the images and determining if defects are present on the substrate 202.

In one embodiment, the lens system 204 includes a purging system such as any of those described previously. As such, the lens system 204 is coupled to a gas source 212 that introduces a gas into the lens system 204. The gas flows through the lens system 204 to a cover 214 that is configured to produce a gas stream in front of the front lens 210 of the lens system 204.

The inspection system 200 also includes a base 216 and an optics plate 218 for supporting the lens system 204 during inspection. The optics plate 218 positions the lens system 204 proximate the substrate 202 so that the lens system 204 may collect light emanating therefrom. The substrate 202 itself is supported by a chuck 220. The chuck 220 is configured to hold the substrate 202 during inspection. By way of example, the chuck 220 may be a vacuum, mechanical, or electrostatic chuck. As shown, the chuck 220 is attached to a stage 222, which is supported by the base 216. The stage 222 is arranged to move the chuck 220 and thus the substrate 202 within a single plane (e.g., X & Y directions) and relative to the optical axis of the lens system 204 so that all or any selected part of the substrate surface may be inspected.

Figure 7:
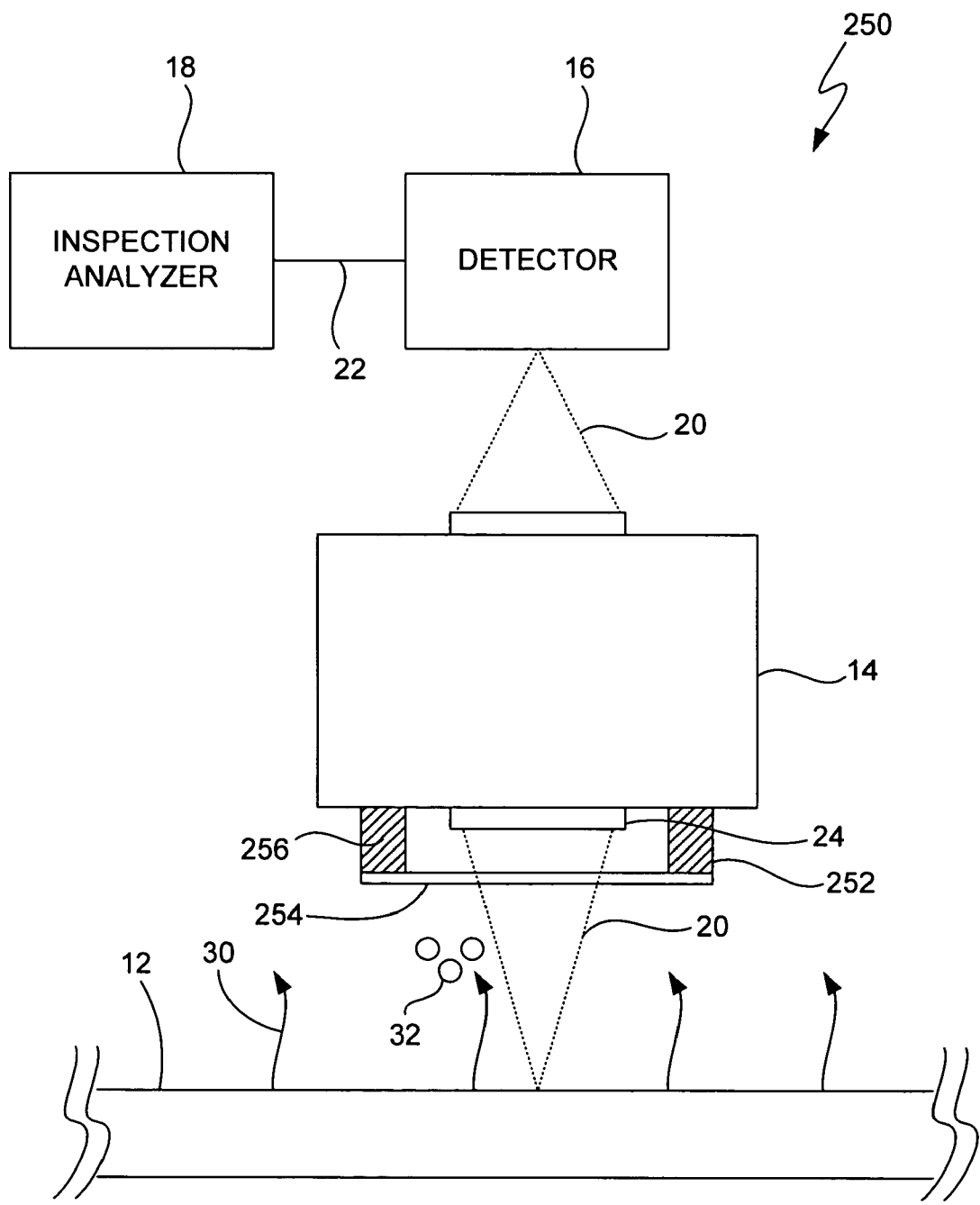
FIG. 7 is a simplified diagram of an optical inspection system, in accordance with another embodiment of the present invention.

FIG. 7 is a simplified diagram of an optical inspection system 250, in accordance with another embodiment of the present invention. This figure is similar to FIG. 1, however instead of using a gas flow system to prevent lens contamination, a transparent cover 252 is used. As shown, the transparent cover 252 is disposed between the optical component 24 and the sample 12. The transparent cover 252 is configured to allow the passage of light so that the light emanating from the sample may be collected while still blocking the contamination 30 that has outgassed from the sample 12. The main purpose of the transparent cover 252 is to keep particles from hitting the optical component 24. The transparent cover 252 is generally configured to be a disposable or replaceable part. That is, overtime the transparent cover 252 may collect deposits and thus it may need to be replaced in order to prevent variations in the inspection, i.e., the deposits may distort the images. In essence, the transparent cover 252 serves as a sacrificial portion of the optical system 14.

The transparent cover 252 generally includes an optical membrane 254 that is secured to a peripheral frame 256. The frame 256 is configured to support the optical membrane 254 and to provide a means for positioning the optical membrane 254 between the optical component 24 and the sample 12. The optical membrane 254, on the other hand, is configured to protect the optical component 24 from contamination while providing a window for light. In most cases, the optical membrane 254 is attached to the upper edge of the peripheral frame 256. The optical membrane 254 may be attached to the frame 256 using any suitable attachment means. By way of example, an adhesive or bonding agent may be used.

The optical membrane 254 may be widely varied. For example, it may be formed from any suitable transparent material that transports UV and does not add to the outgassing problem, i.e., it is preferably formed from materials that have no or a limited amount of outgassing. In one embodiment, the optical membrane 254 is a membrane formed from nitrocelluouse, fluoropolymers, and the like. These materials are used conventionally in forming pellicles. The optical membrane 254 may also be formed from quartz, fused silica or modified fused quartz. Modified fused quartz has been found to work well at wavelengths close to 157 nm. The thickness of the membrane typically varies according to the material used. However, it is generally kept small so as not to induce a lens effect, i.e., if its too thick it may act like a lens thereby causing misfocus and spherical aberrations. By way of example, the thickness may be between about 0.75 and about 3 microns. It should be noted that having a small thickness is not a limitation and that larger thicknesses may be used. However, the optical components are typically redesigned to anticipate or compensate for the effects of using a thick cover. The frame 256, on the other hand, may be formed from any suitable structural material that supports the optical membrane 254 and does not add to the outgassing problem. By way of example, the frame 256 may be formed from metals such as aluminum and stainless steel.

The location of the optical membrane 254 may be widely varied. For example, it may be located close to the optical component 24 (as shown), somewhere between the optical component 24 and the sample 12 or it may be located close to the sample 12. In any of these cases, the optical membrane 254 is preferably placed outside of the focal plane so that the optical membrane 254 and any deposits attached thereto do not negatively impact the image of the sample 12, i.e., there is a higher sensitivity to flaws closer to the focal plane. In the illustrated embodiment, the optical membrane 254 is positioned proximate the optical component 24. The optical membrane 254 via the frame 256 is generally positioned relative to the optical system or the pedestal that supports the sample 12. For example, the frame 256 may rest on a surface of the optical system or the pedestal or it may be attached to the optical system or the pedestal. In the illustrated embodiment, the frame 256 is attached to the optical system 14. The manner in which the frame 256 is attached may be widely varied. For example, it may be attached with screws, magnets, snaps, hooks, locking grooves and the like. The frame 256 itself may also be threaded to the optical system 14 or it may be connected to a flip element that moves the frame 256 in and out of the optical path. The size and shape of the optical membrane 254 may also be widely varied. The size and shape generally depends on the size and shape of the image at the location of the transparent cover 252 in the optical path. In most cases, the optical membrane 254 is at least the size and shape of the imaging area of the optical component 24.

Although the transparent cover 252 is shown attached to the optical system 14, it should be noted that this is not a limitation. For example, referring to FIG. 8, a transparent cover 260 may be attached to (or resting on) a pedestal 262 used to support the sample 12 during inspection. In this particular embodiment, the transparent cover 260 typically spans the dimensions of the sample 12.

Figure 8:
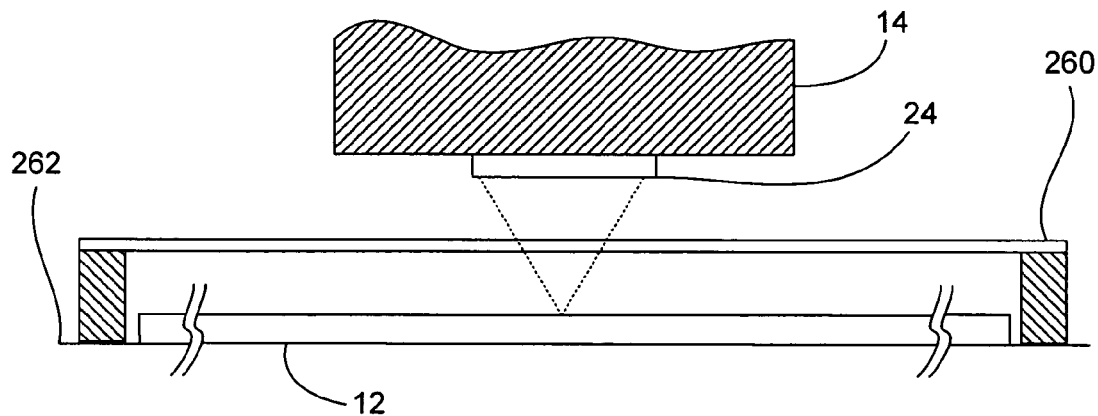
FIG. 8 is a simplified diagram of an optical inspection system, in accordance with another embodiment of the present invention.

Furthermore, although only a single transparent cover is shown in FIGS. 7 and 8, it should be noted that multiple transparent covers may be used to further prevent contamination from reaching the optical components. For example, referring to FIG. 9, a first transparent cover 264 may be positioned relative the optical system 14 and a second transparent cover 266 may be positioned relative the pedestal 262. As should be appreciated, when more than one cover is disposed along the optical path in the system, and/or if other materials with increased optical resistance are inserted in the light path, optical distortion may be introduced into the system, with potential consequences such as scattering, diffraction, undesirable refraction, loss of focus, etc. In order to address such issues, the optical properties of the covers 264 or 266 may be adjusted to compensate for optical distortions. Alternatively or additionally, the optical characteristics of the lenses and light sources in the optical system 14 may be modified to compensate for the disturbances introduced by the covers 264 or 266.

Figure 10:
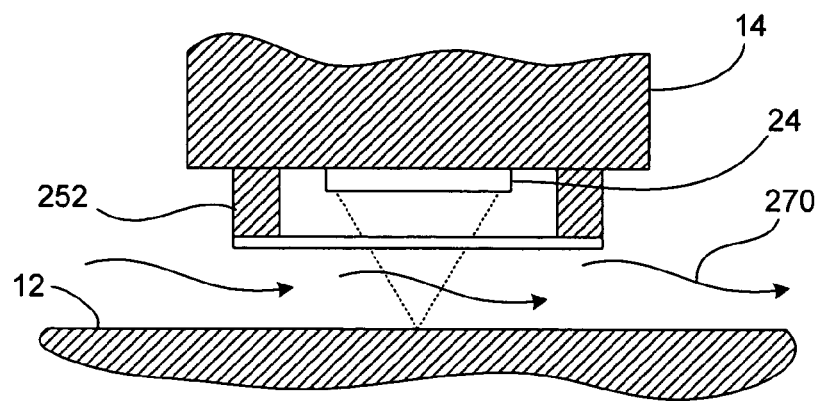
FIG. 10 is a simplified diagram of an optical inspection system, in accordance with another embodiment of the present invention.
Figure 11:
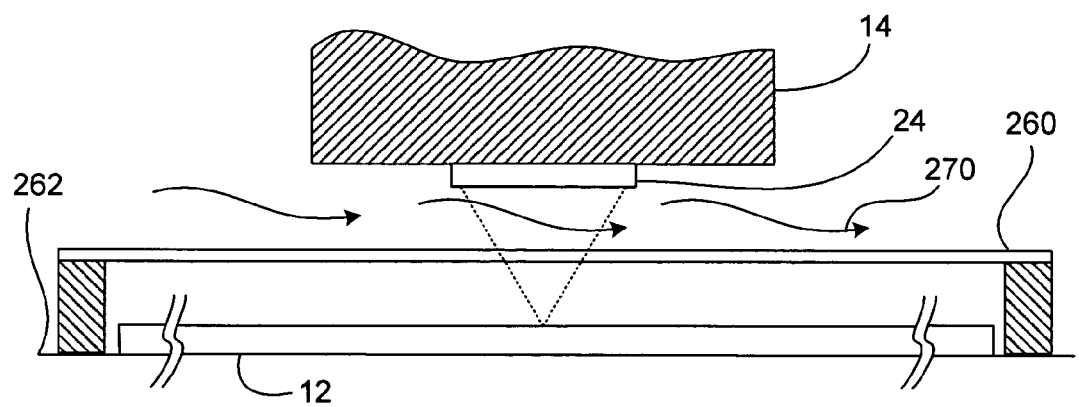
FIG. 11 is a simplified diagram of an optical inspection system, in accordance with another embodiment of the present invention.
Figure 12:
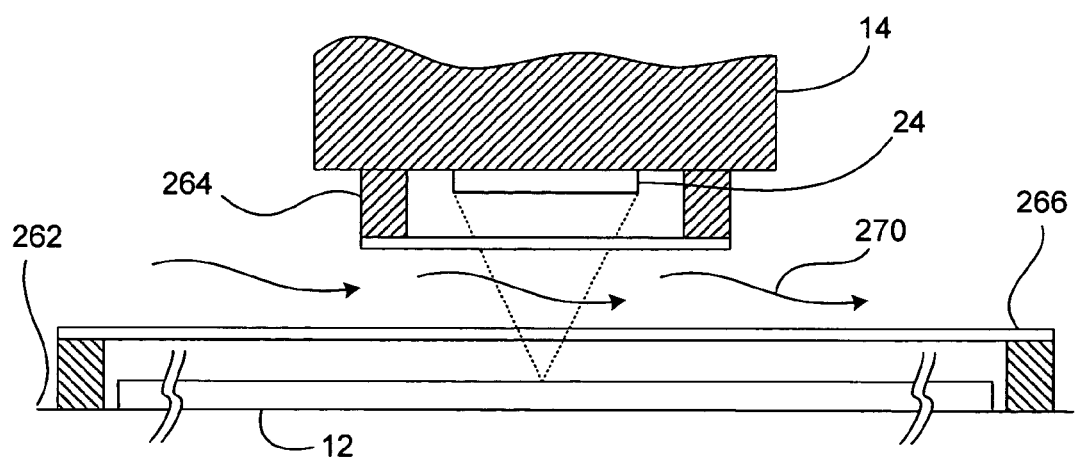
FIG. 12 is a simplified diagram of an optical inspection system, in accordance with another embodiment of the present invention.

In accordance with another embodiment of the invention, single or multiple transparent covers may be used along with the previously described gas flow systems to further prevent contamination from reaching the optical components and possibly to prevent contaminants from depositing on the transparent cover. For example, referring to FIGS. 10, 11 and 12 a gas stream 270 may be used in combination with the transparent covers shown in FIGS. 7, 8 and 9. In FIG. 10, the gas stream 270 flows between the transparent cover 252 and the sample 12. In FIG. 11, the gas stream 270 flows between optical component 24 and the transparent cover 260. In FIG. 12, the gas stream 270 flows between the transparent covers 264 and 266.

Figure 9:
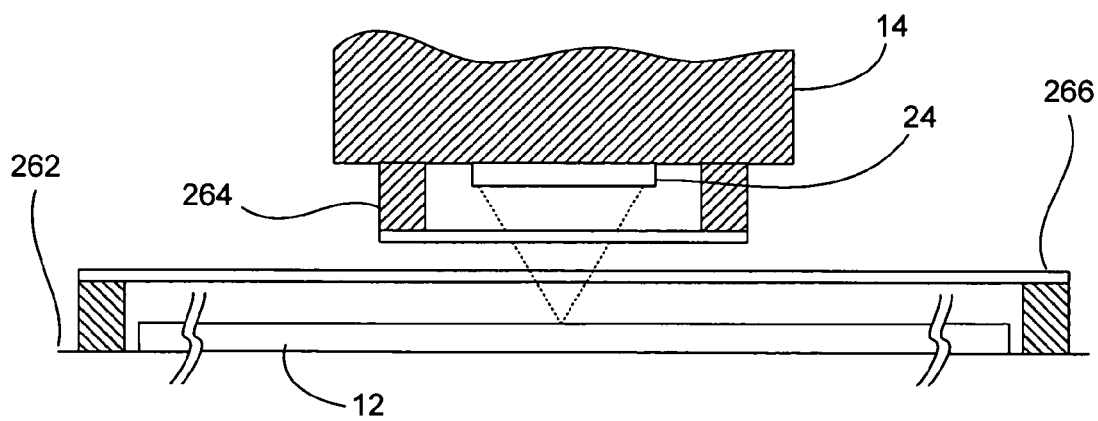
FIG. 9 is a simplified diagram of an optical inspection system, in accordance with another embodiment of the present invention.

More particularly, the gas streams discussed in FIGS. 3, 4 and 5 may be used in combination with the transparent covers shown in FIGS. 7, 8 and 9. In fact, FIGS. 13–15, which are described below, show three possible combinations of these embodiments.

Figure 13:
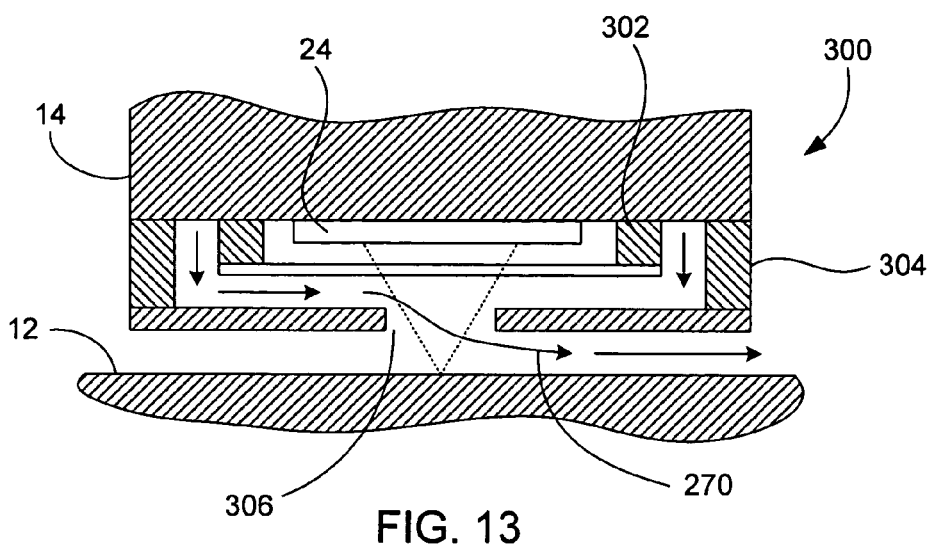
FIG. 13 is a simplified diagram of an optical inspection system, in accordance with another embodiment of the present invention.

FIG. 13 is a side elevation view of a dual protection arrangement 300, in accordance with one embodiment of the present invention. As shown, the dual protection arrangement 300 includes a transparent cover 302 and a lateral gas flow cover 304. By way of example, the transparent cover 302 may correspond to the transparent cover shown in FIG. 7 and the lateral gas flow cover 304 may correspond to the cover shown in FIG. 5. In this particular embodiment, the transparent cover 302 is configured to surround the optical component 24, and the lateral gas flow cover 304 is configured to surround the transparent cover 302. As such, the gas stream 270 flows between the transparent cover 302 and the lateral gas flow cover 304, through an opening 306 in the lateral gas flow cover 304 and between the lateral gas flow cover 304 and the sample 12. In order to form a triple or even quadruple protection arrangement, another transparent cover may be configured to surround the lateral gas flow cover and/or the sample such that multiple membranes are disposed between the sample and the optical component.

Figure 14:
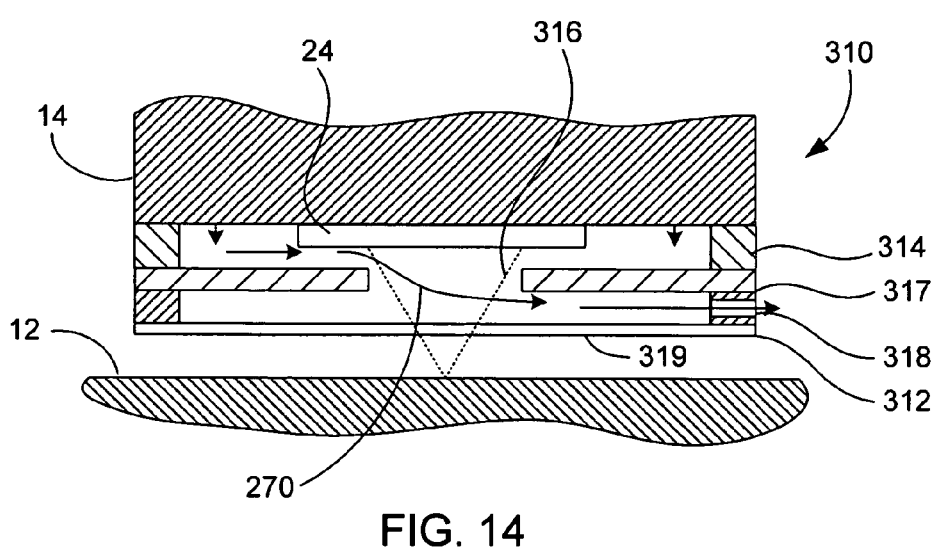
FIG. 14 is a simplified diagram of an optical inspection system, in accordance with another embodiment of the present invention.

FIG. 14 is a side elevation view of a dual protection arrangement 310, in accordance with another embodiment of the present invention. As shown, the dual protection arrangement 310 includes a transparent cover 312 and a lateral gas flow cover 314. By way of example, the transparent cover 312 may correspond to the transparent cover shown in FIG. 7 and the lateral gas flow cover 314 may correspond to the cover shown in FIG. 5. In this particular embodiment, the lateral gas flow cover 314 is configured to surround the optical component 24, and the transparent cover 312 is configured to surround the lateral gas flow cover 314. As such, the gas stream 270 flows between the optical component 24 and the lateral gas flow cover 314, through an opening 316 in the lateral gas flow cover 314 and between the lateral gas flow cover 314 and the transparent cover 312. The frame 317 of the transparent cover 312 may include a passageway 318 for allowing the gas stream to be exhausted away from the inspection area.

Although the membrane 319 of the transparent cover 312 is shown spanning the same distance as the lateral gas flow cover 314, it should be noted that this is not a limitation and that it may span longer or shorter distances. For example, it may only span the dimensions of the opening 316. Furthermore, in order to form a triple protection arrangement, another transparent cover may be configured to surround the sample such that multiple membranes are disposed between the sample and the optical component.

Figure 15:
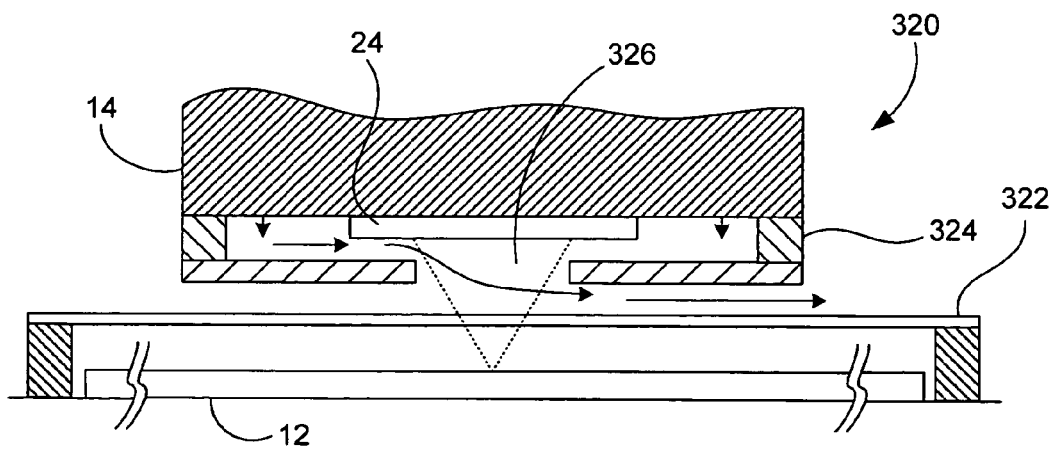
FIG. 15 is a simplified diagram of an optical inspection system, in accordance with another embodiment of the present invention.

FIG. 15 is a side elevation view of a dual protection arrangement 320, in accordance with another embodiment of the present invention. As shown, the dual protection arrangement 320 includes a transparent cover 322 and a lateral gas flow cover 324. By way of example, the transparent cover 322 may correspond to the transparent cover shown in FIG. 8 and the lateral gas flow cover 324 may correspond to the cover shown in FIG. 5. In this particular embodiment, the lateral gas flow cover 324 is configured to surround the optical component 24, and the transparent cover 322 is configured to surround the sample 12. As such, the gas stream 270 flows between the optical component 24 and the lateral gas flow cover 324, through an opening 326 in the lateral gas flow cover 324 and between the lateral gas flow cover 324 and the transparent cover 322.

It should be noted that the embodiments shown in FIGS. 13–15 are not a limitation and that they may vary according to the specific needs of each inspection system. For example, the gas flow cover may correspond to the gas flow covers shown in FIGS. 3 and 4 as well.

While this invention has been described in terms of several preferred embodiments, there are alterations, permutations, and equivalents, which fall within the scope of this invention. For example, although various aspects of the present invention were described in context of inspection systems, it should be understood that they may also be utilized in other systems such as metrology systems and/or lithography systems (e.g., mask and wafer writing). It should also be noted that there are many alternative ways of implementing the methods and apparatuses of the present invention. It is therefore intended that the following appended claims be interpreted as including all such alterations, permutations, and equivalents as fall within the true spirit and scope of the present invention.

What is claimed is:

1. An inspection system for detecting defects on a sample, the inspection system comprising:
    an optical subsystem configured to collect ultra violet light emanating from the sample, the optical subsystem including an optical component having an optical surface;
    a detector configured to receive the collected light from the optical subsystem and to generate an image of at least a portion of the sample with the received light;
    an analyzer configured to determine whether there are any defects present on the portion of the sample by analyzing the image generated by the detector; and
    a gas purge system configured to produce a gas stream that blocks contaminants from reaching the optical surface of the optical component and that transports the contaminants away from the optical surface of the optical component, the gas purge system including a substantially planar cover having an opening disposed in front of and along an optical axis of the optical component, the opening allowing light to pass for the purpose of inspecting the optical surface of the optical component, and the gas stream to pass for the purpose of preventing contaminants from reaching the optical surface of the optical component.

2. The inspection system as recited in claim 1 wherein the optical component is a front collection lens that is the optical component of the optical subsystem that is closest to the sample to be inspected.

3. The inspection system as recited in claim 2 wherein the planar cover is spaced apart from the optical surface of the front collection lens along the optical axis such that a first gas conduit is created between the cover and the optical surface of the front collection lens, wherein the planar cover is spaced apart from the surface of the sample to be inspected along the optical axis such that a second gas conduit is created between the planar cover and the surface of the sample to be inspected, and wherein the gas stream flows through the first conduit to the opening and from the opening through the second conduit.

4. The inspection system as recited in claim 3 further comprising a transparent cover disposed along the optical axis bet the planar cover and the sample to be inspected, the second conduit being created between the planar cover and the transparent cover.

5. The inspection system as recited in claim 2 further comprising a transparent cover disposed along the optical axis between the front collection lens and the planar cover, the planar cover being spaced apart from the transparent cover along the optical axis such that a first gas conduit is created between the planar cover and the transparent cover, wherein the planar cover is spaced apart from the surface of the sample to be inspected along the optical axis such that a second gas conduit is created between the planar cover and the surface of the sample to be inspected, and wherein the gas stream flows through the first conduit to the opening and from the opening through the second conduit.

6. The system as recited in claim 1 further comprising a transparent cover that physically blocks contaminants from reaching the optical surface of the optical component.

7. The system as recited in claim 6 wherein the transparent cover includes an optical membrane and a frame.

8. The system as recited in claim 7 wherein the optical membrane is disposed between the sample and the optical component.

9. The system as recited in claim 1 wherein the sample is associated with semiconductor manufacturing.

10. The system as recited in claim 9 wherein the sample is a reticle, mask or wafer.

11. The system as recited in claim 1 wherein the gas stream flows parallel to the optical component before traveling through the opening.

12. The system as recited in claim 1 wherein the gas stream is symmetrically distributed through the opening.

13. The system as recited in claim 1 wherein the gas stream is asymmetrically distributed through the opening.

14. The system as recited in claim 1 wherein the optical component is a lens.

15. The system as recited in claim 1 wherein the contaminants correspond to hydrocarbons, inorganics or moisture.

16. The inspection system as recited in claim 1 wherein the planar cover is spaced apart from the optical surface of the optical component along the optical axis such that a gas conduit is created between the cover and the optical surface of the optical component, the gas stream flowing through the gas conduit and through the opening in the cover.

17. The inspection system as recited in claim 1 wherein the optical subsystem is disposed inside a housing, and wherein the gas purging system includes a gas source that supplies gas into the housing thereby form the gas stream, the planar cover cooperating with the housing to enclose the optical subsystem such that the gas stream exits through the opening in the planar cover.

18. A system for inspecting substrates, comprising:
an optical subsystem having a front lens; and
a cover disposed between the front lens and the substrate to be inspected, the cover having an opening that allows ultra violet light to pass between the front lens and the substrate to be inspected, the cover defining at least in part a channel within in which a gas stream is created for the purpose of preventing particles from depositing on the front lens.

19. The system as recited in claim 18 wherein the channel creates a lateral gas stream that travels across the optical axis of the front lens.

20. The system as recited in claim 19 wherein the cover includes a top surface and a bottom surface, the top surface including a collection recess for collecting a purge gas flowing around the optical subsystem and a direction recess for directing the collected gas to the opening, the bottom surface including an exit recess for collecting the gas passing though the opening and for directing the gas to an exhaust area outside the periphery of the front lens, the exit recess being located directly across from the direction recess, the gas stream flowing through and across the opening from the top surface to the bottom surface between the direction recess on the top surface and the exit recess on the bottom surface.

21. The system as recited in claim 20 wherein the depth of the collection recess and direction recess is smaller than the depth of the exit recess.

22. The system as recited in claim 20 wherein the distance between the top surface and the front lens is smaller than the distance between the bottom surface and the substrate.

23. The system as recited in claim 20 wherein the collection recess includes a feeding portion and a capturing portion, the capturing portion is configured to collect gas and the feeding portion is configured to feed the captured gas to the direction recess.

24. The system as recited in claim 20 wherein the capturing portion forms a semi annular channel along the periphery of the cover, and the feeding portion forms a flared channel connecting the capturing portion to the direction recess.

25. The system as recited in claim 19 wherein the cover includes a first channel and a second channel, the first channel being recessed in a top surface of the cover, the second channel being recessed in a bottom surface of the cover, the first channel being located on one side of the opening, the second channel being located on the other side of the opening, an end of the first channel aligning with the a beginning of the second channel, the gas stream flowing through and across the opening between the end of the first channel and the beginning of the second channel.

26. A gas flow system for an optical inspection system, the gas flow system comprising:
a means for flowing a gas stream in front of an exposed optical surface of the optical inspection system so as to prevent contaminants from adversely effecting the exposed optical surface of the optical inspection system,
wherein the gas stream is routed across the exposed optical surface substantially transverse to the optical axis of the exposed optical surface.

27. The system as recited in claim 26 wherein the optical surface is associated with a lens capable of directing UV light.

28. The system as recited in claim 26 wherein flowing a gas stream in front of the exposed optical surface effectively removes the contaminants in a region proximate the exposed optical surface.

29. A gas flow system for an optical inspections system, the gas flow system comprising:
  a means for flowing a gas stream in from of an exposed optical surface of the optical inspection system so as to prevent contaminants from adversely effecting the exposed optical surface of the optical inspection system,
  wherein the gas stream is routed away from the exposed optical surface substantially parallel to the optical axis of the optical surface.

30. An optical inspection system for inspecting a semiconductor surface for defects or other abnormalities thereof, comprising:
  an optical subsystem configured to collect light emanating from the semiconductor surface and to direct the collected light to a detector, the optical subsystem including a series of optical components a lens disposed along an optical path, the series of optical components including a front collection lens that is the optical component closest to the semiconductor surface; and
  a transparent cover disposed proximately to the front collection lens between the front collection lens and the semiconductor surface to protect the front collection lens from contamination.

31. A gas flow system for an optical inspection system, the gas flow system comprising:
  a means for flowing a gas stream in front of an exposed optical surface of the optical inspection system so as to prevent contaminants from adversely effecting the exposed optical surface of the optical inspection system,
  wherein the optical inspection system includes an optical subsystem having a plurality of optical components aligned along an optical axis, the optical components cooperating to collect light emanating from a sample and to direct the collected list to a detector for the purpose of defect analysis, and wherein the exposed optical surface is from at least one of the optical components of the optical inspection system, and
  wherein the gas steam flows at least in part parallel to the exposed surface.

* * * * *

UNITED STATES PATENT AND TRADEMARK OFFICE
CERTIFICATE OF CORRECTION

PATENT NO.        : 7,138,640 B1
APPLICATION NO. : 10/688839
DATED             : November 21, 2006
INVENTOR(S)       : Delgado et al.

It is certified that error appears in the above-identified patent and that said Letters Patent is hereby corrected as shown below:

In line 3 of claim 4 (column 17, line 18) change "bet" to --between--.

In line 1 of claim 29 (column 19, line 5) change "inspections" to --inspection--.

In line 3 of claim 29 (column 19, line 8) change "in from" to --in front--.

In line 12 of claim 31 (column 20, line 17) change "list" to --light--.

In line 16 of claim 31 (column 20, line 21) change "steam" to --stream--.

Signed and Sealed this

Sixth Day of November, 2007

JON W. DUDAS
*Director of the United States Patent and Trademark Office*